United States Patent [19]

Landry et al.

[11] Patent Number: 5,527,349
[45] Date of Patent: Jun. 18, 1996

[54] PHOTOCHEMOTHERAPY DOSIMETER

[75] Inventors: Robert J. Landry, Mt. Airy; Stephanie Matchette, Silver Spring; Glenn N. Merberg, Gaithersburg, all of Md.

[73] Assignee: The United States of America as represented by the Secretary of the Department of Health and Human Services, Washington, D.C.

[21] Appl. No.: 463,665

[22] Filed: Jun. 5, 1995

Related U.S. Application Data

[62] Division of Ser. No. 188,331, Jan. 25, 1994, Pat. No. 5,441,530.

[51] Int. Cl.$^6$ .................................................. A61B 5/00
[52] U.S. Cl. ........................... 607/88; 607/90; 128/634; 128/664; 250/370.070
[58] Field of Search .................. 609/86–94; 128/633–4, 128/664–6; 250/370.07

[56] References Cited

U.S. PATENT DOCUMENTS

| | | |
|---|---|---|
| 4,986,671 | 1/1991 | Sun et al. . |
| 5,000,901 | 3/1991 | Lyer et al. . |
| 5,037,615 | 8/1991 | Kane . |
| 5,119,463 | 6/1992 | Vurek et al. . |
| 5,275,160 | 1/1994 | Lilge et al. . |
| 5,330,718 | 7/1994 | Hui et al. . |
| 5,441,530 | 8/1995 | Landry et al. ............................ 607/88 |

FOREIGN PATENT DOCUMENTS

| | | |
|---|---|---|
| 0352610 | 1/1990 | European Pat. Off. . |
| WOA8600514 | 1/1986 | WIPO . |

Primary Examiner—Angela D. Sykes
Assistant Examiner—Robert L. Nasser, Jr.
Attorney, Agent, or Firm—Lowe, Price, LeBlanc & Becker

[57] ABSTRACT

A photochemotherapy dosimeter for monitoring cumulative photochemotherapy radiation dosage. The photochemotherapy dosimeter includes an optical fiber having a chemical cell attached at one end thereof. The chemical cell contains a photobleachable chemical which can be in a solution or incorporated into a matrix material. Changes in the absorption of the photobleachable chemical are used to monitor the cumulative photochemotherapy radiation dosage. In use, the chemical cell of the photochemotherapy dosimeter is positioned near an abnormal tissue which is subjected to photochemotherapy treatment.

4 Claims, 2 Drawing Sheets

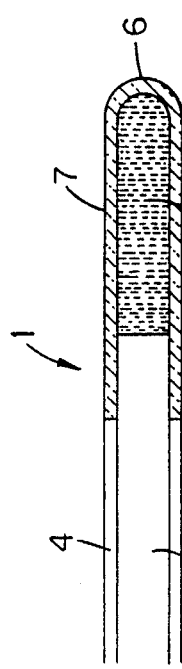
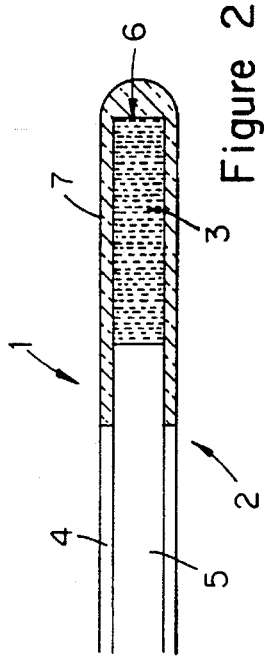
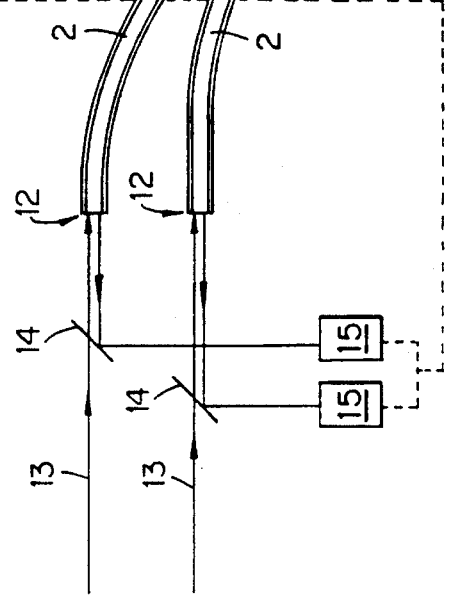

PHOTOCHEMOTHERAPY DOSIMETER

This application is a division of application Ser. No. 08/188,331 filed Jan. 25, 1994, now U.S. Pat. No. 5,441,530.

TECHNICAL FIELD

The present invention relates to photochemotherapy procedures and devices used in such procedures. More particularly, the present invention relates to photochemotherapy dosimeters which provide a direct measurement of cumulative dosages of optical radiation at a remote situs.

BACKGROUND ART

In photochemotherapy for the treatment of non-superficial tumors, the patient is treated with a photosensitizing drug and optical radiation. The drug, which is generally administered to the patient 2 to 3 days before exposure to optical radiation, is absorbed in both normal and abnormal tissues throughout the body. However, the photosensitizing drug is retained for longer periods of time in tumor tissue as compared to most normal healthy tissue. Thus, over time, tumor tissue retains a higher concentration of the drug than does normal tissue.

The drug that is retained in the tissue provides for increased optical radiation absorption at selected wavelengths. This is referred to as photosensitization. The absorption of a sufficient amount of optical radiation following tissue photosensitization can result in tissue death.

Successful photochemotherapy treatment is dependent on the delivery of a sufficient amount of optical radiation to the entire tumor volume. For this reason, interstitial fiber optic applicators are used to deliver optical radiation inside deep seated tumors. However, the delivery of an excessive amount of optical radiation to the area of the tumor can result in unwanted damage to nearby photosensitized non-targeted normal healthy tissue. Thus, it is important to deliver an optimum amount of optical radiation to the tumor area, while avoiding overexposure and excessive damage to nearby or adjacent healthy tissue.

For this purpose, interstitial fiber optic dosimeters are used to monitor the optical radiation dose at strategically located sites within the tumor or near the tumor boundaries.

Present day dosimeters have certain disadvantages related to the manner in which they measure either the fluency of the treatment optical radiation directly or the fluorescence that it produces in a detector material. In either case, the fluency signal must be integrated over time in order to obtain a measure of cumulative dose. Thus, present day dosimeters do not provide a direct measurement of the cumulative dose. Another disadvantage with present day dosimeters is that the intensity of the signal they produce for measurement purposes is so low that it is often difficult to measure or detect at all. Because the intensity of the optical radiation at the treatment site to be measured is not very strong, treatment time can be as long as tens of minutes to several hours. Consequently, there is considerable uncertainty in the integrated value which is conventionally used to determine the cumulative dose. For these reasons, the accuracy of present day photochemotherapy dosimeter devices is limited.

The present invention provides a new and improved device for the measurement of optical radiation dose during photochemotherapy for the treatment of non-superficial deep-seated tumors.

DISCLOSURE OF THE INVENTION

It is according one object of the present invention to provide a photochemotherapy dosimeter for measuring optical radiation at a remote situs.

Another object of the present invention is to provide a photochemotherapy dosimeter for measuring cumulative optical radiation at a remote situs over time.

A further object of the present invention is to provide a method of monitoring photochemotherapy treatment at a remote situs.

A further object of the present invention is to provide a method of monitoring photochemotherapy treatment at a remote situs which involves measuring a cumulative dose of optical radiation over time.

A still further object of the present invention is to provide an apparatus for delivering photochemotherapy to a remote situs.

A yet further object of the present invention is to provide an apparatus for delivering photochemotherapy to a remote situs which includes means to monitor optical radiation at the remote situs.

According to these and other objects of the present invention which will become apparent as the description thereof proceeds, the present invention provides a photochemotherapy dosimeter which includes an optical fiber having a proximal end and a distal end;

a chemical cell attached to the distal end of the optical fiber, the chemical cell having a reflective surface which faces the optical fiber; and a photobleachable chemical provided within the chemical cell.

The present invention further provides an apparatus for performing photochemotherapy which includes:

at least one optical treatment fiber for delivering photochemotherapy radiation to a remote situs; and at least one photochemotherapy dosimeter having an optical fiber and a chemical cell attached to an end of the optical fiber which chemical cell contains a photobleachable chemical for receiving photochemotherapy radiation from the at least one optical treatment fiber.

Also provided by the present invention is a method of monitoring photochemotherapy during the treatment of abnormal tissue which involves:

directing photochemotherapy radiation to an abnormal tissue;

providing at least one photochemotherapy dosimeter having an optical fiber and a chemical cell attached to an end of the optical fiber which chemical cell contains a photobleachable chemical;

positioning the at least one photochemotherapy dosimeter near the abnormal tissue so that the chemical cell of the at least one photochemotherapy dosimeter receives the photochemotherapy radiation; and detecting changes in absorption of the photobleachable chemical in the chemical cell.

BRIEF DESCRIPTION OF DRAWINGS

The present invention will be described with reference to the attached drawings which are given by way of non-limiting examples only, in which:

FIG. 1 is schematic cross sectional view of a photochemotherapy dosimeter according to the present invention.

FIG. 2 is a schematic cross sectional view of a photochemotherapy dosimeter according to another embodiment of the present invention.

FIG. 3 is a schematic illustration of an apparatus in which the photochemotherapy dosimeter is used during photochemotherapy according to the present invention.

BEST MODE FOR CARRYING OUT THE INVENTION

Figure 4:
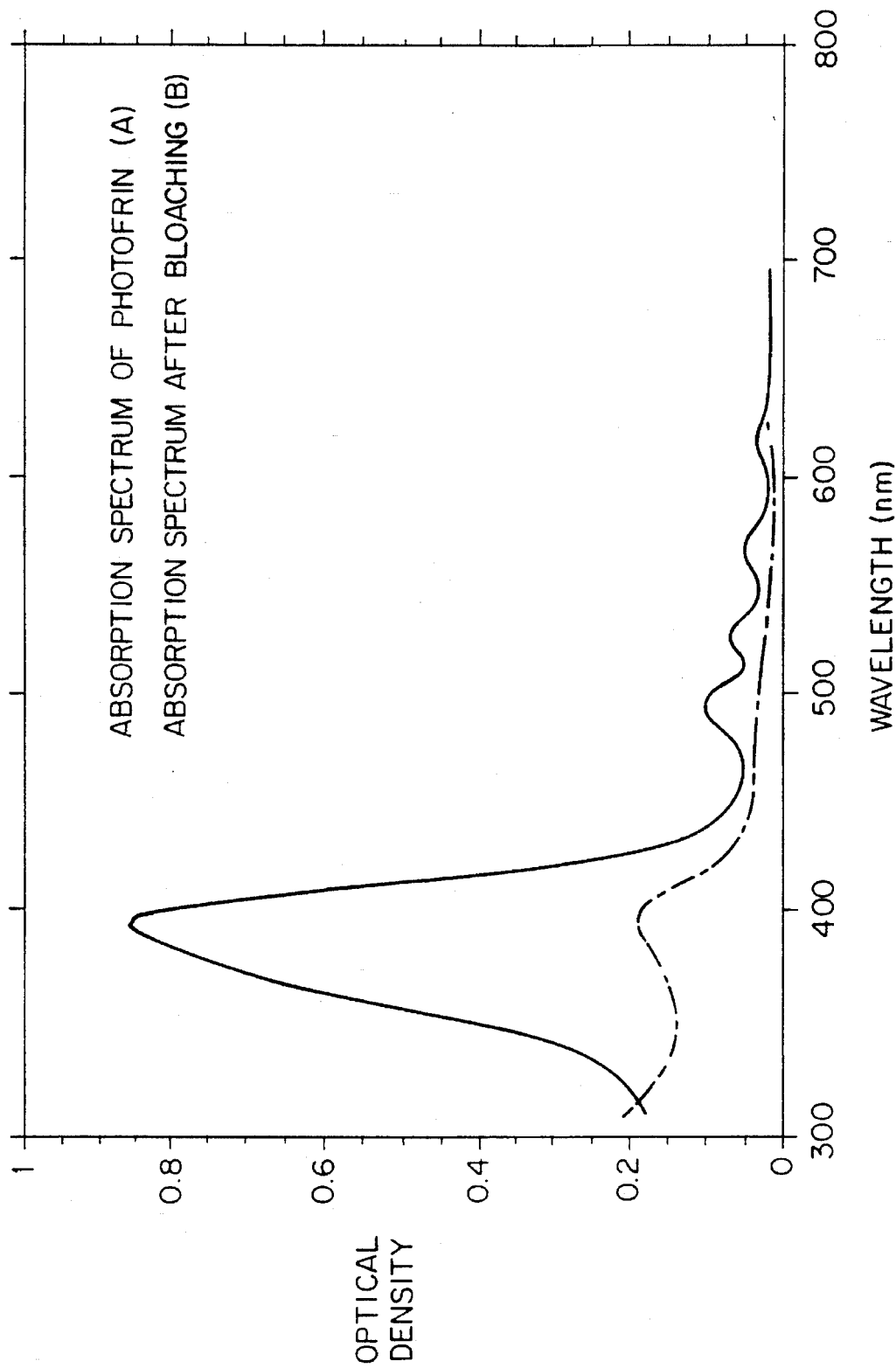
FIG. 4 is a graph which shows the absorption spectrum of 4 μg/ml solution of Photofrin in 0.1 mg/ml Triton X-100 following 77% photobleaching.

The present invention utilizes a unique combination of fiber optic principles in conjunction with principles of photochemistry. The device provided and used according to the present invention is an insertable probe that is made up of an optical fiber and an integrated fiber optic chemical cell attached to a distal end of the optical fiber.

The chemical cell contains an optical radiation absorbing chemical which is capable of undergoing photobleaching. Photobleaching is a process in which the absorption of an optical photon or photons by a chromophore results in the annihilation of the chromophore, and a resulting change in color or absorption.

The chemical cell is attached to the distal end of the optical fiber and is designed to receive irradiation transmitted through the optical fiber and to reflect received irradiation backwards through the optical fiber in such a manner that, within the chemical cell, the irradiation traverses a distance which is twice the length of the chemical cell. After passing through the chemical cell, the reflected irradiation is directed onto the distal end of the optical fiber, so as to be received and transmitted backwards through the optical fiber. When used in photochemotherapy dosimetry, one or more of the fiber optic chemical cells of the present invention are strategically located within a tumor or at the tumor boundaries. Although the chemical cells are particularly designed for use within or adjacent a tumor or other cellular structure, it is also possible to locate the chemical cell(s) outside of a subject's body.

According to one embodiment of the present invention the dosimeter is operated in the following manner. Pulsed optical radiation of an appropriate wavelength is transmitted down the length of the fiber and through the chemical cell which contains a predetermined concentration of the photobleachable chemical.

During photochemotherapy treatment, the chemical cell is exposed to the photochemotherapy optical radiation which causes photobleaching of the optical radiation absorbing chemical therein. The pulsed optical radiation is periodically transmitted down the fiber to measure the absorption of the chromophore in the chemical cell. Because the absorption of optical radiation is proportional to the concentration of the chromophore, a change in the absorption provides a measure of the change in the chromophore. Thus, the concentration of the photobleaching chromophore can be determined, from which the optical radiation dose can be deduced.

FIG. 1 is a schematic cross sectional view of a photochemotherapy dosimeter according to the present invention. As shown in FIG. 1 the photochemotherapy dosimeter 1 includes an optical fiber 2 which is of a suitable length so as to allow insertion of the distal end into a remote situs, e.g., adjacent or within superficial tumor tissue of a subject, and connection of the proximal end to an optical pulse generator and radiation detector. The outside diameter of the optical fiber 2 should be selected so that there is minimum damage when the dosimeter is inserted into a tissue situs. A practical diameter for optical fiber 2 can be 5 mm or less. In applications in which the photochemotherapy dosimeter is inserted by using a standard biocompatible catheter, the outside diameter should be chosen based upon the size of the catheter.

A chemical cell 3 is attached to the distal end of the optical fiber 2. As shown, the chemical cell 3 is preferably axially aligned with the optical fiber 2, and has an outside diameter which is equal to that of the optical fiber 2.

The optical fiber 2 shown in FIG. 1 includes a conventional cladding layer 4 and a fiber core 5. The function of the cladding layer 4 is to ensure that optical radiation directed through the optical fiber 2 is internally reflected within the fiber core 5 and does not escape through the sides of the optical fiber 2.

The chemical cell 3 includes a reflective surface 6 at the distal end thereof. The reflective surface 6 can be provided on the surface of the chemical cell 3, or in the inner surface of a transparent covering 7 which covers the chemical cell 3. In a preferred embodiment, the reflective surface 6 is curved as shown in FIG. 1. In this regard, the reflective surface 6 can be curved in such a manner to focus radiation toward the center of the fiber core and thus avoid a situation in which reflected radiation escapes through the transparent covering 7. In an alternative embodiment, the reflective surface 6 can be planar and perpendicular to the common axis of the optical fiber 2 and chemical cell 3 as shown in FIG. 2. The reflective surface 6 can be made by applying a layer of a reflective material such as silver, gold, or the like by conventional deposition processes, such as sputtering, vapor deposition, etc. Alternatively, a thin film of a metallic foil of a reflective material can be secured to the inside or outside of the transparent covering 7.

The material from which the optical fiber core 5 is made can be selected from any conventional material, including fused silica, quartz, PCS, plastic, and the like. Likewise, the cladding layer 4 can be made of any conventional cladding material which is biocompatible. The transparent covering 7 can be made of any biocompatible transparent material which will contain the optical radiation absorbing chemical in the chemical cell 3 and allow exposure of the radiation absorbing chemical to the photochemotherapy treatment radiation. In this regard, it is noted that the chemical cell 3 can either be a chamber defined by the transparent covering 7 which contains the optical radiation absorbing chemical in a solution, or a support matrix which is impregnated with the optical radiation absorbing chemical, e.g. a porous glass doped or impregnated with the optical radiation absorbing chemical.

As discussed above, the optical radiation absorbing chemical comprises a photobleachable chemical having a predetermined concentration of a photobleachable chromophore. The concentration of photobleachable chromophore is chosen such that: (1) there is a substantial absorption of the radiation at the pulsed optical radiation wavelength (generally between 300 and 700 nm, and preferably between 300 and 450 nm), (2) the pulse reflected from the distal end of the chemical cell is of sufficient signal strength to be easily detected, and (3) a known amount of the chromophore is irreversibly photobleached by the treatment optical radiation. Suitable concentrations depend on the chromophore used and the required sensitivity. Such concentrations can be readily determined utilizing standard calibration methods. For example, in one embodiment a concentration of 4 µg/ml Photofrin (Quadra Logic Tech., Vancouver, B.C.) was found to produce an absorption spectrum with an optical density peak from about 300 to 450 nm and a detectable optical density from 300 to about 650 nm.

Other requirements for the photobleachable chemical to be used in the cell are that the photobleachable chemical be photobleachable by the optical radiation used for the photochemotherapy and that the photobleachable chemical be stable over a period of time of several hours.

One particular photobleachable chemical found to be useful for purposes of the present invention is Photofrin. Photofrin or a similar photobleachable chemical with an appropriate chromophore can serve as the photobleachable chemical in the chemical cell of the present invention. Examples of suitable photobleachable chemicals include porphyrins (complexed and non-complexed), phthalocyanins and chlorins. The particular selection of the photobleachable chemical would be based upon the particular wavelength used in the photochemotherapy. Such wavelengths are known and have already been established by others.

FIG. 3 is a schematic illustration of an apparatus in which the photochemotherapy dosimeter is used during photochemotherapy according to the present invention.

In FIG. 3 a tumor tissue mass 8 is illustrated as being within the body 9 of a subject and being surrounded by healthy normal tissue 10. Treatment optical radiation is transmitted to the tumor mass 8 through a plurality of interstitial optical treatment fibers 11 in a conventional manner.

A plurality of photochemotherapy dosimeters 1 according to the present invention are inserted within the subject's body 9 so that the chemical cells 3 of the photochemotherapy dosimeters 1 are within or adjacent the tumor mass 8.

The proximal end 12 of each optical fiber 2 of the photochemotherapy dosimeters 1 receives pulsed optical radiation 13 from a suitable source such as a laser and a beam chopper (not shown), The frequency of the pulsed optical radiation is such that the one pulse is allowed to be received by the optical radiation detectors 15 before a subsequent optical pulse is sent through the proximal end 12 of the optical fibers 2. The pulsed optical radiation (hereafter referred to as "interrogator pulsed radiation") passes through a beam splitter 14 or similar functioning device prior to entering the proximal end 12 of each optical fiber 2. As depicted by the arrows in FIG. 3, the interrogator pulsed radiation passed through the beam splitters 14 and into the proximal ends 12 of the optical fibers 2. The interrogator pulsed radiation passes through the optical fibers 2 and through the photobleachable chemical within the chemical cells 3. After passing through the chemical cells 3, the interrogator pulsed radiation is reflected by the reflective surface in the chemical cells 3 and backwards through the photobleachable chemical, the optical fibers 2, and out the proximal ends 12 of the optical fibers 2. The reflected interrogator pulsed radiation is directed by the beam splitters 14 to interrogator optical radiation detectors 15. The interrogator optical radiation detectors 15 can include photodiodes or other known optical detectors. The interrogator optical radiation detectors 15 detect changes in the absorption of the photobleachable chemical which provides a measure of the change in the concentration of the photobleaching chromophore, from which the optical radiation dose of the photochemotherapy can be deduced, by known calibration techniques.

For convenience, any photobleaching caused by absorption of the interrogator optical pulse can be taken into account during the calibration of the interrogator pulse system. The interrogator pulse can also consist of optical radiation at two wavelengths. In this case, radiation at one wavelength is selected so that it is absorbed by the photobleachable chromophore while radiation at the other wavelength is selected so that it is not absorbed by the chromophore. The radiation at the non-absorbed wavelength can serve as a reference signal for the radiation at the wavelength that is absorbed. The ratio of the radiation at the two wavelengths reflected back from the chemical cell to the detector will provide a stable signal that is independent of any artifacts which may be induced during radiation transport in the fiber and chemical cell. Fox example, artifacts may result from changes in the index of refraction of the tissue being treated, which may result in coupling interrogator pulse radiation out of time fiber or chemical cell in an unpredictable manner.

According to a further embodiment of the present invention the chemical cells of photochemotherapy dosimeters can be located within the tumor and used to control the exposure duration. In this case, a control signal is generated by the interrogator optical radiation detectors and used to control, e.g., increase, decrease or turn off the photochemotherapy optical treatment radiation in any one or all of the treatment fibers 11. Such control, as indicated by the dashed line in FIG. 3, can be based upon the concentration level of the photobleachable chromophore in one or more of the chemical cells.

FIG. 4 is an example of the absorption spectrum of a 4 µg/ml solution of Photofrin in 0.1 mg/ml Triton X-100 following 77% photobleaching at a wavelength of 488 nm. The spectra were obtained utilizing a Carey spectrophotometer. Alternatively, any radiation absorbed by the Photofrin will produce the photobleaching. Thus, radiation at 630 nm which is typically used during photochemotherapy produces detectable photobleaching.

The photochemotherapy dosimeters of the present invention can be fabricated by etching the cladding from one end of the optical fiber and permanently attaching the chemical cell to the core of the fiber exposed from the etched cladding. The chemical cell can be attached to the optical fiber by a suitable optical cement alone and/or held in position by the transparent covering which is attached to the optical fiber core.

In an alternative embodiment, the chemical cell can be fabricated from porous glass in which one end of the optical fiber is saturated with the photobleaching chemical solution and permanently covered with heat shrink transparent plastic tubing. In this embodiment, the porous glass tip is prepared in the following way. The fiber tip is first heat treated to produce phase separation. One of the separated phases is then chemically etched to produce the pores in the fiber, which are subsequently impregnated with a photobleachable chromophore by dipping or soaking the porous fiber in a solution containing a photobleachable chromophore.

In the case of a sodium borosilicate glass fiber, after the cladding layer is etched or mechanically removed from a small end portion of the fiber, the fiber can be phase separated by heat treatment at about 560° C. for about 6 hours. The heat treatment divides the glass fiber into two phases—one that is rich in silica and one that is rich in sodium boron oxide. Next the borate rich phase can be leached away by contacting the heat treated fiber in a solution of 2 N hydrochloric acid. This process leaves a silica rich porous fiber skeleton which can be impregnated with a photobleachable chromophore by dipping or soaking the porous fiber in a solution containing the photobleachable chromophore.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

We claim:

1. A method of monitoring photochemotherapy during treatment of abnormal tissue which comprises:

directing photochemotherapy radiation to an abnormal tissue;

providing at least one photochemotherapy dosimeter having an optical fiber and a chemical cell attached to an end of said optical fiber which chemical cell contains a photobleachable chemical;

positioning said at least one photochemotherapy dosimeter near said abnormal tissue so that said chemical cell of said at least one photochemotherapy dosimeter receives said photochemotherapy radiation; and detecting changes in optical radiation absorption of said photobleachable chemical in said chemical cell.

2. A method of monitoring photochemotherapy during treatment of abnormal tissue according to claim 1, wherein said photochemotherapy radiation directed to said abnormal tissue is controlled in response to said detected changes in optical radiation absorption of said photobleachable chemical in said chemical cell.

3. A method of monitoring photochemotherapy during treatment of abnormal tissue according to claim 1, wherein said optical radiation absorption is detected from an optical interrogator pulse which passes through said photochemotherapy dosimeter.

4. A method of monitoring photochemotherapy during treatment of abnormal tissue according to claim 1, wherein said abnormal tissue comprises a non-superficial tumor.

* * * * *